United States Patent [19]  [11]  4,349,685
Dunbar  [45]  Sep. 14, 1982

[54] 5-SUBSTITUTED-BENZOXATHIOL-2-ONES

[75] Inventor: Joseph E. Dunbar, Midland, Mich.

[73] Assignee: The Dow Chemical Company, Midland, Mich.

[21] Appl. No.: 296,761

[22] Filed: Aug. 27, 1981

[51] Int. Cl.$^3$ ............................................. C07D 327/04
[52] U.S. Cl. ...................................... 549/33; 424/276
[58] Field of Search ........................................... 549/33

[56] References Cited

U.S. PATENT DOCUMENTS 2,332,418  10/1943  Werner .................................. 549/33

FOREIGN PATENT DOCUMENTS 823251  11/1959  Fed. Rep. of Germany .

OTHER PUBLICATIONS

Burton et al., J. Chem. Soc., 1952, pp. 2193–2196.

Primary Examiner—Richard Raymond

[57] ABSTRACT

Novel, biologically active, 5-substituted-1,3-benzoxathiol-2-ones are prepared by the reaction of 5-hydroxy-1,3-benzoxathiol-2-one with a substituted isocyanate in the presence of an activating agent and an appropriate organic solvent. The novel compounds are suitable for use as fungicides and as the active constituents in fungicidal compositions.

7 Claims, No Drawings

5-SUBSTITUTED-BENZOXATHIOL-2-ONES

BACKGROUND OF THE INVENTION

The present invention discloses a novel class of biologically active 5-substituted-1,3-benzoxathiol-2-ones, with the 5 position having various substituted carbamate groups. These compounds are useful as foliage fungicides.

SUMMARY OF THE INVENTION

This invention is directed to a group of novel, biologically active 5-substituted-1,3-benzoxathiol-2-ones corresponding to the formula:

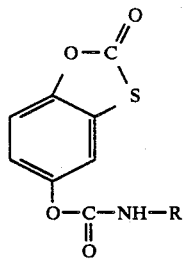

wherein R is lower alkyl, substituted aryl, haloalkyl, carbalkoxyalkylene, and alkylcarbonyloxyalkylene.

As used herein, the term "lower alkyl" means saturated, aliphatic radicals including straight and branched chain radicals of from one to about four carbon atoms inclusive, such as methyl, ethyl, propyl, isopropyl, n-butyl isobutyl, sec-butyl or tert-butyl; the term "alkylene" refers to aliphatic, straight or branched chain radicals of from one to about four carbon atoms inclusive, such as methylene, ethylene, propylene and the like; the term "substituted aryl" means a phenyl radical monosubstituted with a halo, trihalomethyl, or lower alkyl group. The halogen required for the halo-substituted aryl may be, for example, chlorine, fluorine, bromine or iodine. The halogens required for the trihalomethyl substituent may be independently selected from the group consisting of chlorine, fluorine, bromine or iodine; the term "haloalkyl" refers to a lower alkyl group monosubstituted with a halogen wherein the halogen may be, for example, chlorine, bromine, fluorine or iodine; the term "carbalkoxyalkylene" refers to a radical of the formula:

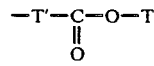

wherein T is lower alkyl, and T' is alkylene; the term "alkylcarbonyloxyalkylene" refers to a radical of the formula:

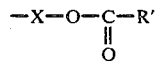

wherein X is alkylene, and R' is methyl, ethyl, ethylene or isopropenyl (1-methylvinyl) forming radicals such as acetyloxymethylene, propionyloxyethylene, acryloyloxyethylene, methacryloyloxyethylene and the like.

The compounds of the present invention are suitable for use as fungicides. Typically, the compounds are effective against the causative organisms of rice blast, wheat leaf rust and downey mildew. Some of the compounds also show activity as urease inhibitors.

The compounds of the present invention may be prepared by the reaction of 5-hydroxy-1,3-benzoxathiol-2-one (prepared as described by H. Burton and S. B. David, J. Chem. Soc. 1952, 2193) of the formula:

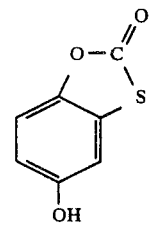

with a substituted isocyanate of the formula:

wherein R may be lower alkyl, substituted aryl, haloalkyl, carbalkoxyalkylene or alkylcarbonyloxyalkylene. The reaction is carried out in an appropriate solvent such as methyl ethyl ketone, methylene chloride, acetonitrile, tetrahydrofuran, toluene, ethyl ether, 2-hexanone or dimethylformamide. Reaction temperatures can run from about ambient temperature to about 115° C. Some substituted isocyanates will react with phenolic hydroxyl groups above that temperature; however, some carbamate products undergo reaction reversal at higher temperatures. The reaction is carried out in the presence of a small amount of activating agent such as triethylamine or dibutyltin dilaurate. Conveniently, the reactants are then heated at reflux temperature for about one to about six hours. The solvent is then removed from the reaction mixture by conventional techniques such as filtration, decantation, or evaporation. The residue may then be recrystallized from various solvents such as toluene, ethyl acetate, methylcyclohexane, carbon tetrachloride and combinations thereof, such as ethyl acetate in methylcyclohexane. In general, the purified products are white or colorless crystalline solids.

DETAILED DESCRIPTION

The following examples are merely illustrative and are not intended to limit the invention.

EXAMPLE 1

5-[2-(Propionyloxy)ethylcarbamoyloxy]-1,3-benzoxathiol-2-one 5-hydroxy-1,3-benzoxathiol-2-one (16.8 grams) was mixed with 2-(isocyanato)ethyl propionate (15.0 grams) and 10 drops of dibutyltin dilaurate in 200 milliliters of methyl ethyl ketone. The resulting solution was heated at reflux temperature for four hours and fifteen minutes, after which the solvent was removed by evaporation in vacuo, leaving a brown, viscous oil which crystallized upon standing at room temperature for 10 to 15 hours. The crude product was twice recrystallized from toluene. The purified compound, 5-[2-(propionyloxy)ethylcarbamoyloxy]-1,3-benzoxathiol-2-one, was a white, fibrous crystalline substance with a melting point of 78°–79° C. Elemental analysis calculated for $C_{13}H_{13}NO_6S$ (percent): carbon—50.15; hydrogen—4.21; nitrogen—4.50. Found: carbon—50.4; hydrogen—4.27; nitrogen—4.45.

EXAMPLE 2

5-[3-(Trifluoromethyl)phenylcarbamoyloxy]-1,3-benzoxathiol-2-one 5-hydroxy-1,3-benzoxathiol-2-one (16.8 grams) was mixed with 3-(trifluoromethyl)phenyl isocyanate (18.7 grams) and 1.01 grams of triethylamine in 200 milliliters of methyl ethyl ketone. This solution was heated at reflux temperature for one hour, after which the solvent was removed by evaporation in vacuo. The resulting residue was recrystallized twice from ethyl acetate, leaving the desired purified product, 5-[3-(trifluoromethyl)phenylcarbamoyloxy]-1,3-benzoxathiol-2-one. The product was a white crystalline solid which exhibited a melting point of 166.5°–168° C. Elemental analysis calculated for $C_{15}H_8F_3NO_4S$ (percent): carbon—50.71; hydrogen—2.27; nitrogen—3.94. Found: carbon—51.0; hydrogen—2.29; nitrogen—4.11.

EXAMPLE 3

5-[(Carbethoxymethyl)carbamoyloxy]-1,3-benzoxathiol-2-one 5-hydroxy-1,3-benzoxathiol-2-one (14.0 grams), was mixed with ethyl isocyanatoacetate (11.9 grams) and 0.84 gram of triethylamine in 165 milliliters of methyl ethyl ketone. The resulting mixture was then heated at reflux temperature for one hour and ten minutes and was allowed to cool and stand at ambient temperature for 15 hours. The solvent was then removed by evaporation in vacuo. The white, solid residue was recrystallized from a solution of 2% ethyl acetate in carbon tetrachloride. The resulting white crystalline solid had a melting point of 94.5°–96.5° C. This product was then recrystallized from a mixture of ethyl acetate and methylcyclohexane to give the desired purified product, 5-[(carbethoxymethyl)-carbamoyloxy]-1,3-benzoxathiol-2-one as colorless crystals having a melting point of 97.5°–98.5° C. Elemental analysis calculated for $C_{12}H_{11}NO_6S$ (percent): carbon—48.48; hydrogen—3.73; nitrogen—4.71. Found: carbon—48.6; hydrogen—3.84; nitrogen—4.80.

EXAMPLE 4

5-[(3-Ethylphenyl)carbamoyloxy]-1,3-benzoxathiol-2-one 5-hydroxy-1,3-benzoxathiol-2-one (15.0 grams) was mixed with 3-ethylphenyl isocyanate (13.1 grams) in 180 milliliters of methyl ethyl ketone in the presence of 0.90 gram of triethylamine. This solution was heated at reflux temperature with stirring for 3 hours and 15 minutes. The solvent was then removed by evaporation in vacuo and the residual, viscous oil was dissolved in a hot mixture of ethyl acetate and methylcyclohexane. Upon slowly cooling to room temperature, the solution gave the purified 5-[(3-ethylphenyl)carbamoyloxy]-1,3-benzoxathiol-2-one as a white crystalline solid with a melting point of 96°–97° C. Elemental analysis calculated for $C_{16}H_{13}NO_4S$ (percent): carbon—60.94; hydrogen—4.15; nitrogen—4.44. Found: carbon—61.2; hydrogen—4.26; nitrogen—4.54.

EXAMPLE 5

5-(n-Butylcarbamoyloxy)-1,3-benzoxathiol-2-one 5-hydroxy-1,3-benzoxathiol-2-one (14.3 grams) was mixed with n-butyl isocyanate (8.85 grams) in 175 milliliters of methyl ethyl ketone in the presence of 1.3 milliliters of triethylamine. The reaction mixture was then heated at reflux temperature for 2.5 hours. The solvent was then removed from the reaction mixture by evaporation in vacuo. The off-white solid residue was recrystallized from toluene and the purified product, 5-(n-butylcarbamoyloxy)-1,3-benzoxathiol-2-one was obtained, as a white, fluffy, crystalline solid with a melting point of 99°–100° C. Elemental analysis calculated for $C_{12}H_{13}NO_4S$ (percent): carbon—53.92; hydrogen—4.90; nitrogen—5.24. Found: carbon—54.1; hydrogen—4.89; nitrogen—5.27.

EXAMPLE 6

5-[(2-Chloroethyl)carbamoyloxy]-1,3-benzoxathiol-2-one 5-hydroxy-1,3-benzoxathiol-2-one (14.0 grams) was mixed with 2-chloroethyl isocyanate (8.79 grams) in 170 milliliters of methyl ethyl ketone in the presence of 0.84 gram of triethylamine. The resulting mixture was heated at reflux temperature with stirring for 6 hours and 20 minutes. The solvent was then removed by evaporation in vacuo. The residue was recrystallized from carbon tetrachloride (containing a small amount of ethyl acetate). A subsequent recrystallization from toluene gave the purified product, 5-[(2-chloroethyl)carbamoyloxy]-1,3-benzoxathiol-2-one, as a white crystal line solid with a melting point of 105.5°–107.5° C. Elemental analysis calculated for $C_{10}H_8ClNO_4S$ (percent): carbon—43.88; hydrogen—2.95; nitrogen—5.12. Found: carbon—43.7; hydrogen—3.13; nitrogen—5.37.

In accordance with the present invention, it has been discovered that the 5-substituted-1,3-benzoxathiol-2-ones disclosed herein can be utilized as fungicides. While not all compounds of the present invention may be equally effective at similar concentrations, all of the compounds exhibit either fungicidal or fungus controlling activity. Typically, they are effective in the control of the causative organisms of rice blast, wheat leaf rust, downey mildew and the like. For such uses, one or more of the compounds can be employed in unmodified form as a dust, or as a spray in aqueous suspensions formulated either as wettable powders, or concentrates for dilution. In other procedures, the compounds may be dissolved in water or acetone, and then diluted with water to be employed as a spray.

The exact concentration of the compound to be employed in the treating compositions is not critical and may vary considerably provided the fungal organisms are contacted with an effective amount of the compound. As used herein, the term "effective amount" refers to that amount of compound which causes fungicidal or fungus controlling effects on the causative organisms of diseases such as rice blast, wheat leaf rust, downey mildew and the like. Good results are obtained when compositions containing fungicidal or fungas controlling concentrations of the compounds are employed. For such purposes, compositions containing from about 25 to about 1,200 parts per million by weight of one or more of the compounds are effective.

In a representative operation, substantially complete kill (99 percent) of the causative organism of rice blast was achieved when 5-[(2-chloroethyl)carbamoyloxy]-1,3-benzoxathiol-2-one was employed as the sole compound in an aqueous suspension at a concentration of 75 parts per million by weight of the ultimate dispersion.

In another representative operation, substantially complete kill of the causative organism of wheat leaf rust was obtained when 5-[2-(propionyloxy)ethylcarbamoyloxy]-1,3-benzoxathiol-2-one was employed as the sole compound formulated into an aqueous suspension at a concentration of 300 parts per million by weight of the ultimate dispersion.

In another operation, the compound 5-[(3-ethylphenyl)carbamoyloxy]-1,3-benzoxathiol-2-one exhibited substantial control of the causative organism of downey mildew. Solutions containing 500 parts per million by weight of the compound were formulated and applied to the host plants through two different modes of administration. First, the solution was applied to the root system of the host plants by drenching the chemicals into the pots or by placing the pots into larger cups containing the solution of the compound. Second, a foliar chemical treatment was applied to the host plants. The plants were then exposed to the pathogen and placed under conditions suitable for infection and development of the disease. The compound exhibited a 90 percent control of the causative organism of downey mildew.

In another representative operation, either 5-[3-(trifluoromethyl)phenylcarbamoyloxy)]-1,3-benzoxathiol-2-one or 5-[(carbethoxymethyl)carbamoyloxy]-1,3-benzoxathiol-2-one showed 100 percent urease inhibition when used individually in in vitro testing methods. Solutions of the compounds were prepared at a concentration of 25 parts per million. To these were added solutions of jack bean urease. The mixtures were incubated overnight at 37° C. Subsequent colorimetric testing of the solutions showed 100 percent inhibition of the urease on the test mixture.

What is claimed is:

1. A compound corresponding to the formula:

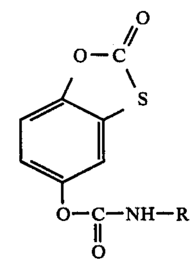

wherein R represents a lower alkyl, substituted aryl, haloalkyl, carbalkoxyalkylene or an alkyl carbonyloxyalkylene group.

2. The compound of claim 1 which is 5-[2-(Propionyloxy)ethylcarbamoyloxy]-1,3-benzoxathiol-2-one.

3. The compound of claim 1 which is 5-[3-(Trifluoromethyl)phenylcarbamoyloxy]-1,3-benzoxathiol-2-one.

4. The compound of claim 1 which is 5-[(Carbethoxymethyl)carbamoyloxy]-1,3-benzoxathiol-2-one.

5. The compound of claim 1 which is 5-[(3-Ethylphenyl)carbamoyloxy]-1,3-benzoxathiol-2-one.

6. The compound of claim 1 which is 5-(n-Butylcarbamoyloxy)-1,3-benzoxathiol-2-one.

7. The compound of claim 1 which is 5-[(2-Chloroethyl)carbamoyloxy]-1,3-benzoxathiol-2-one.

* * * * *